(12) United States Patent
Adinolfi (10) Patent No.: US 11,197,675 B2
(45) Date of Patent: Dec. 14, 2021

(54) POSITIONING GUIDE FOR SURGICAL INSTRUMENTS AND SURGICAL INSTRUMENT SYSTEMS

(71) Applicant: Covidien LP, Mansfield, MA (US)

(72) Inventor: Amanda M. Adinolfi, Wallingford, CT (US)

(73) Assignee: COVIDIEN LP, Mansfield, MA (US)

( * ) Notice: Subject to any disclaimer, the term of this patent is extended or adjusted under 35 U.S.C. 154(b) by 180 days.

(21) Appl. No.: 16/720,235

(22) Filed: Dec. 19, 2019

(65) Prior Publication Data

US 2021/0186509 A1 Jun. 24, 2021

(51) Int. Cl.
| | | |
|---|---|---|
| *A61B 17/10* | (2006.01) | |
| *A61N 1/375* | (2006.01) | |
| *A61B 17/068* | (2006.01) | |
| *A61B 34/35* | (2016.01) | |
| *A61B 17/064* | (2006.01) | |
| *A61N 1/36* | (2006.01) | |

(52) U.S. Cl.
CPC ............ *A61B 17/10* (2013.01); *A61B 17/068* (2013.01); *A61N 1/37518* (2017.08); *A61B 34/35* (2016.02); *A61B 2017/0647* (2013.01); *A61N 1/3605* (2013.01)

(58) Field of Classification Search
CPC .................. A61B 17/10; A61B 17/068; A61B 2017/0647; A61N 1/37518
See application file for complete search history.

(56) References Cited

U.S. PATENT DOCUMENTS

| | | |
|---|---|---|
| 3,596,528 A | 8/1971 | Dittrich et al. |
| 3,866,510 A | 2/1975 | Eibes et al. |
| 4,350,491 A | 9/1982 | Steuer |
| 4,730,726 A | 3/1988 | Holzwarth |
| 4,884,572 A | 12/1989 | Bays et al. |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |

(Continued)

FOREIGN PATENT DOCUMENTS

| | | |
|---|---|---|
| EP | 0374088 A1 | 6/1990 |
| EP | 1721575 A2 | 11/2006 |

(Continued)

OTHER PUBLICATIONS

Extended European Search Report issued in corresponding European Application No. 20215041.3 dated Apr. 23, 2021, 10 pages.

(Continued)

*Primary Examiner* — Nathaniel C Chukwurah
(74) *Attorney, Agent, or Firm* — Carter, DeLuca & Farrell LLP (57) ABSTRACT

A surgical instrument system includes a surgical fastener applier and a positioning guide. The positioning guide includes an implant guide. The implant guide defines a guide channel configured to receive a portion of an implant to support the implant relative to the end effector to enable the surgical fastener applier to fire one or more fasteners through the implant for securing the implant to tissue.

20 Claims, 5 Drawing Sheets

(56) References Cited

U.S. PATENT DOCUMENTS

| | | |
|---|---|---|
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,402,780 B2 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,357,287 B2 | 4/2008 | Shelton, IV et al. |
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |
| 7,670,362 B2 | 3/2010 | Zergiebel |
| 7,740,159 B2 | 6/2010 | Shelton, IV et al. |
| 7,758,612 B2 | 7/2010 | Shipp |
| 7,811,312 B2 | 10/2010 | Stevens et al. |
| 7,819,884 B2 | 10/2010 | Lee et al. |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,913,892 B2 | 3/2011 | Cole et al. |
| 7,922,061 B2 | 4/2011 | Shelton, IV et al. |

(56) References Cited

U.S. PATENT DOCUMENTS

| | | |
|---|---|---|
| 7,922,063 B2 | 4/2011 | Zemlok et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,006,365 B2 | 8/2011 | Levin et al. |
| 8,034,076 B2 | 10/2011 | Criscuolo et al. |
| 8,062,306 B2 | 11/2011 | Nobis et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,152,820 B2 | 4/2012 | Mohamed et al. |
| 8,181,840 B2 | 5/2012 | Milliman |
| 8,216,254 B2 | 7/2012 | McLean et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,333,776 B2 | 12/2012 | Cheng et al. |
| 8,343,176 B2 | 1/2013 | Criscuolo et al. |
| 8,343,184 B2 | 1/2013 | Blier |
| 8,377,044 B2 | 2/2013 | Coe et al. |
| 8,382,773 B2 | 2/2013 | Whitfield et al. |
| 8,382,778 B2 | 2/2013 | Criscuolo et al. |
| 8,414,627 B2 | 4/2013 | Corradi et al. |
| 8,424,740 B2 | 4/2013 | Shelton, IV et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,603,135 B2 | 12/2013 | Mueller |
| 8,613,729 B2 | 12/2013 | Sage et al. |
| 8,672,209 B2 | 3/2014 | Crainich |
| 8,684,247 B2 | 4/2014 | Scirica et al. |
| 8,685,044 B2 | 4/2014 | Bolduc et al. |
| 8,690,889 B2 | 4/2014 | Colesanti et al. |
| 8,690,897 B2 | 4/2014 | Bolduc |
| 8,728,098 B2 | 5/2014 | Daniel et al. |
| 8,728,099 B2 | 5/2014 | Cohn et al. |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,894,669 B2 | 11/2014 | Nering et al. |
| 8,920,439 B2 | 12/2014 | Cardinale et al. |
| 8,926,637 B2 | 1/2015 | Zergiebel |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,345,462 B2 | 5/2016 | Weitzner et al. |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,231 B2 | 6/2016 | Wenchell |
| 9,364,274 B2 | 6/2016 | Zergiebel |
| 9,386,983 B2 | 7/2016 | Swensgard et al. |
| 9,402,623 B2 | 8/2016 | Kayan |
| 9,445,814 B2 | 9/2016 | Ranucci et al. |
| 9,486,218 B2 | 11/2016 | Criscuolo et al. |
| 9,526,498 B2 | 12/2016 | Reed |
| 9,615,830 B2 | 4/2017 | Ranucci et al. |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,783,329 B2 | 10/2017 | Sniffin et al. |
| 9,788,833 B2 | 10/2017 | Zergiebel et al. |
| 2003/0009441 A1 | 1/2003 | Holsten et al. |
| 2004/0092937 A1 | 5/2004 | Criscuolo et al. |
| 2005/0222665 A1 | 10/2005 | Aranyi |
| 2006/0129152 A1 | 6/2006 | Shipp |
| 2007/0038220 A1 | 2/2007 | Shipp |
| 2007/0088390 A1 | 4/2007 | Paz et al. |
| 2007/0106317 A1 | 5/2007 | Shelton et al. |
| 2007/0162030 A1 | 7/2007 | Aranyi et al. |
| 2008/0097523 A1 | 4/2008 | Bolduc et al. |
| 2008/0312687 A1 | 12/2008 | Blier |
| 2009/0112234 A1 | 4/2009 | Crainich et al. |
| 2009/0118776 A1 | 5/2009 | Kelsch et al. |
| 2010/0010294 A1* | 1/2010 | Conlon ............... A61B 1/3132 600/104 |
| 2010/0270354 A1 | 10/2010 | Rimer et al. |
| 2011/0022065 A1 | 1/2011 | Shipp |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2014/0005678 A1 | 1/2014 | Shelton, IV et al. |
| 2014/0014707 A1 | 1/2014 | Onukuri et al. |
| 2014/0200587 A1 | 7/2014 | Pompee et al. |
| 2014/0236196 A1 | 8/2014 | Colesanti et al. |
| 2014/0243855 A1 | 8/2014 | Sholev et al. |
| 2014/0276967 A1 | 9/2014 | Fischvogt et al. |
| 2015/0005748 A1 | 1/2015 | Sniffin et al. |
| 2015/0032130 A1 | 1/2015 | Russo |
| 2015/0133970 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |
| 2016/0007996 A1 | 1/2016 | Bolduc |
| 2016/0074034 A1 | 3/2016 | Shipp |
| 2016/0166255 A1 | 6/2016 | Fischvogt |
| 2016/0249912 A1 | 9/2016 | Fischvogt |
| 2016/0270778 A1 | 9/2016 | Zergiebel |
| 2016/0270835 A1 | 9/2016 | Reed |
| 2016/0278766 A1 | 9/2016 | Wenchell et al. |
| 2016/0338694 A1 | 11/2016 | Kayan |
| 2016/0345967 A1 | 12/2016 | Sniffin et al. |

FOREIGN PATENT DOCUMENTS

| | | |
|---|---|---|
| EP | 2528518 A2 | 12/2012 |
| EP | 2762091 A2 | 8/2014 |
| JP | 09149906 | 6/1997 |
| WO | 2009073754 A2 | 6/2009 |
| WO | 2011145091 A1 | 11/2011 |
| WO | 2013046115 A1 | 4/2013 |
| WO | 2016141183 A1 | 9/2016 |
| WO | 2018071409 A1 | 4/2018 |

OTHER PUBLICATIONS

Extended European Search Report corresponding to EP 14 15 8946.5, completed Jun. 20, 2014 and dated Jul. 8, 2014; (9 pp).

Extended European Search Report corresponding to EP 14 17 8107.0, completed Nov. 24, 2014 and dated Dec. 3, 2014; (5 pp).

Extended European Search Report corresponding to EP 14 17 4656.0, completed Jan. 16, 2015 and dated Jan. 26, 2015; (7 pp).

Extended European Search Report corresponding to EP 14 18 4907.5, completed Jan. 12, 2015 and mailed Jan. 27, 2015; (9 pp).

European Search Report corresponding to EP 14 18 1900.3, completed Mar. 31, 2015 and dated Apr. 9, 2015; 7pp.

Extended European Search Report corresponding to EP 14 19 7885.8 dated Apr. 30, 2015.

Extended European Search Report corresponding to EP No. 11 25 0549.0, completed Sep. 9, 2013 and dated Sep. 17, 2013; 9 pages.

Extended European Search Report corresponding to EP 14 15 9394.7, completed Apr. 16, 2014 and dated Apr. 29, 2014; 8 pages.

European Search Report corresponding to EP 10 01 2659.8, completed Dec. 21, 2010; dated Jan. 3, 2011; 3 pages.

(56) References Cited

OTHER PUBLICATIONS

European Search Report corresponding to EP 10 01 2646.5, completed Feb. 11, 2011; dated Feb. 22, 2011.
Extended European Search Report corresponding to EP 14 15 1663.3 dated Jun. 7, 2016.
Supplementary European Search Report corresponding to EP 14 81 7036 dated Feb. 2, 2017.
European Search Report corresponding to EP 17 15 7259.7 dated May 10, 2017.
Extended European Search Report issued in corresponding European Application No. 18154121.0 dated Oct. 19, 2018.

* cited by examiner

POSITIONING GUIDE FOR SURGICAL INSTRUMENTS AND SURGICAL INSTRUMENT SYSTEMS

BACKGROUND

Many surgical procedures are performed through small incisions in an effort to reduce a patient's trauma and recovery time. Such procedures are generally referred to as minimally invasive. During a typical minimally invasive procedure, surgical instruments with end effectors, which may be robotic or handheld instruments, are inserted into the patient's body to access a target site in the patient's body, for example, to secure an implant at the target site.

SUMMARY

According to one aspect, this disclosure is directed to a surgical instrument system including a surgical fastener applier and a positioning guide. The surgical fastener applier includes an end effector configured to support one or more fasteners. The positioning guide is selectively mountable to the end effector. The positioning guide includes an implant guide. The implant guide defines a guide channel configured to receive a portion of an implant to support the implant relative to the end effector to enable the surgical fastener applier to fire the one or more fasteners through the implant for securing the implant to tissue.

In embodiments, the positioning guide may include an elongated body with the implant guide supported on a distal end portion of the elongated body. The elongated body may include an arched configuration that defines a passage therethrough positioned to receive the end effector.

In various embodiments, the positioning guide may include a distal abutment configured to act as a limit stop for the end effector when the positioning guide is mounted on the end effector. The positioning guide may include a guide rib supported on the distal abutment.

In some embodiments, the implant guide may have a C-shaped configuration.

In certain embodiments, the positioning guide may have a tubular configuration.

In embodiments, the guide channel is configured to receive one or more wings of the implant. The guide channel is configured to position an aperture defined through the one or more wings of the implant so that the aperture receives the one or more fasteners therethrough.

In various embodiments, the surgical fastener applier may be a tack applier and the one or more fasteners may include one or more tacks.

According to another aspect, this disclosure is directed to a positioning guide for a surgical instrument. The positioning guide includes an elongated body defining a passage therethrough configured to receive an end effector of the surgical instrument therein. The elongated body has a proximal end portion and a distal end portion. The distal end portion supports an implant guide. The implant guide defines a guide channel configured to receive a portion of an implant to support an aperture of the implant in registration with a longitudinal axis of the end effector.

In embodiments, the elongated body may have a tubular configuration.

In various embodiments, the elongated body may include a rail extending along an outer surface thereof. The rail may be connected to the implant guide.

According to yet another aspect, this disclosure is directed to an endoscopic surgical tack applier system. The endoscopic surgical tack applier system includes an endoscopic surgical tack applier and a positioning guide. The endoscopic surgical tack applier includes an end effector configured to support one or more tacks. The positioning guide is selectively removable from the end effector. The positioning guide includes an implant guide configured to support an implant adjacent to a distal end portion of the end effector such that an aperture of a wing of the implant is disposed in registration with the one or more tacks when the one or more tacks are supported by the end effector.

In embodiments, at least the implant guide may include a C-shaped cross-section.

The details of one or more aspects of this disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of this disclosure and, together with a general description of this disclosure given above, and the detailed description of the embodiment(s) given below, serve to explain the principles of this disclosure, wherein.

DETAILED DESCRIPTION

Embodiments of this disclosure are described in detail with reference to the drawings, in which like reference numerals designate identical or corresponding elements in each of the several views. As commonly known, the term "clinician" refers to a doctor (e.g., a surgeon), a nurse, or any other care provider and may include support personnel. Additionally, the term "proximal" refers to the portion of structure that is closer to the clinician and the term "distal" refers to the portion of structure that is farther from the clinician.

In the following description, well-known functions or constructions are not described in detail to avoid obscuring this disclosure in unnecessary detail.

With reference to FIGS. 1-8, a surgical fastener applier 10, which may be an endoscopic surgical instrument such as a surgical tack applier, generally includes a handle assembly 12, an elongate shaft assembly 14 that extends distally from handle assembly 12, and an end effector 16 supported on distal end portion of elongated shaft assembly 14. End effector 16 is operable to fire one or more fasteners 30 therefrom upon an actuation of a movable handle 12a relative to a stationary handle 12b of handle assembly 12. Fasteners 30, which may be in the form of tacks, can include any suitable tack such as a standard purchase tack or a deep purchase tack.

Surgical fastener applier 10 can be provided as part of a surgical system. The surgical system further includes an implant 40 and/or a positioning guide 50. Positioning guide 50, which may be in the form of a positioning guide cuff, is selectively attachable to an outer surface of end effector 16 of surgical fastener applier 10 to facilitate positioning of implant 40 relative to end effector 16 for consistently and accurately firing fasteners 30 through implant 40 to secure implant 40 to tissue "T" (see FIGS. 4-8) such as lumbar fascia. Positioning guide 50 may be removably attached to an outer surface of end effector 16 using any suitable technique such as snap-fit, slide-on, friction-fit, clip-on, etc.

Figure 1:
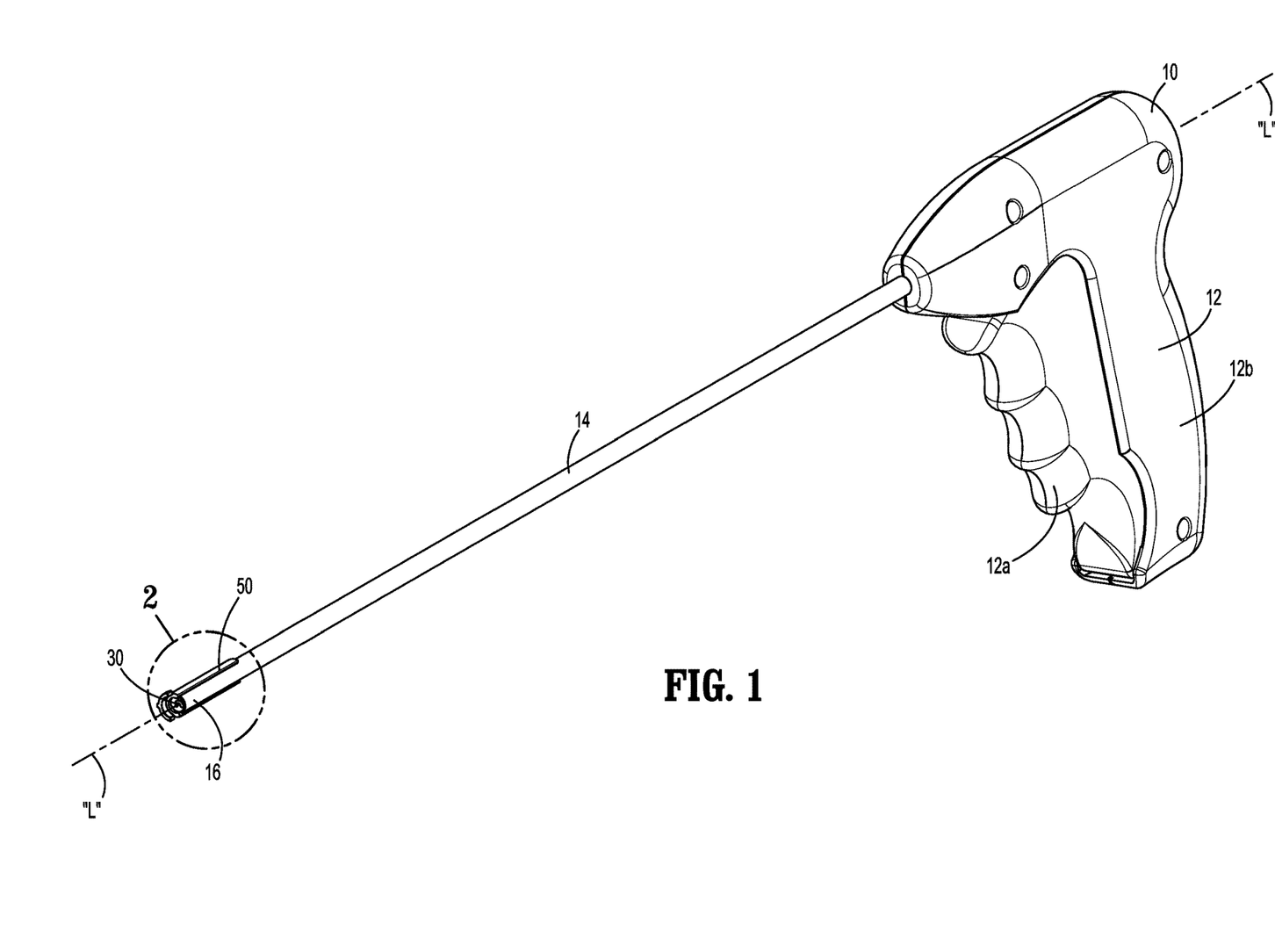
FIG. 1 is a perspective view of one embodiment of a positioning guide supported on a surgical instrument in accordance with the principles of this disclosure.
Figure 2:
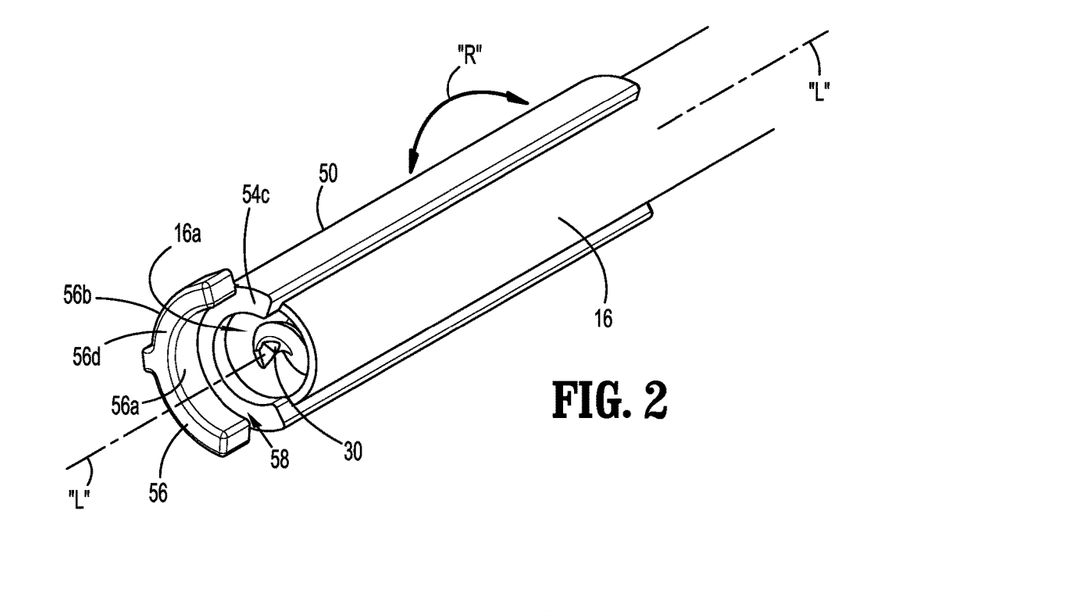
FIG. 2 is an enlarged view of the indicated area of detail shown in FIG. 1.
Figure 3:
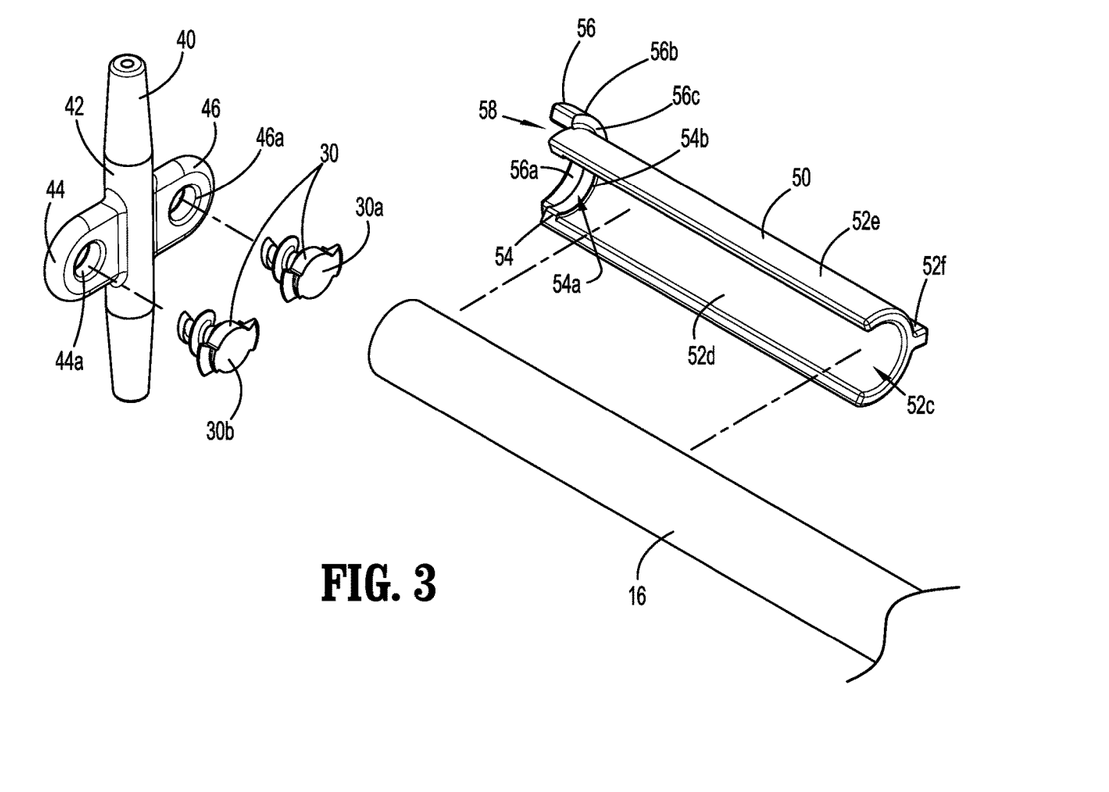
FIG. 3 is a perspective view, with parts separated, of one embodiment of a surgical instrument system including the positioning guide and the surgical instrument of FIG. 1 as well as an implant and fasteners.
Figure 4:
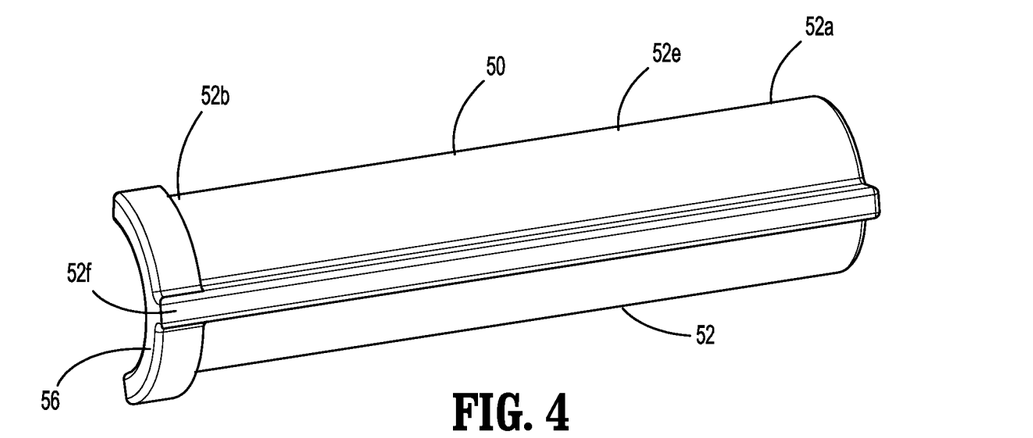
FIG. 4 is an enlarged, perspective view of the positioning guide shown in FIG. 1.
Figure 5:
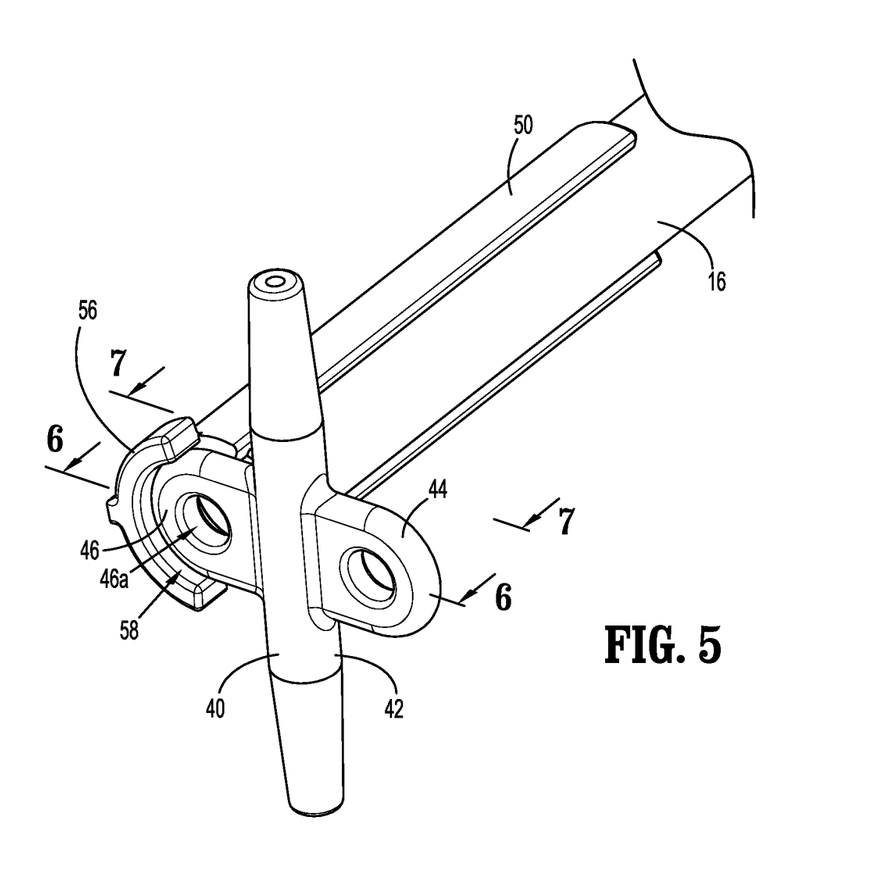
FIG. 5 is a perspective view of the surgical instrument system of FIG. 3 illustrating the positioning guide positioning the implant relative to the surgical instrument thereof.
Figures 6, 7:
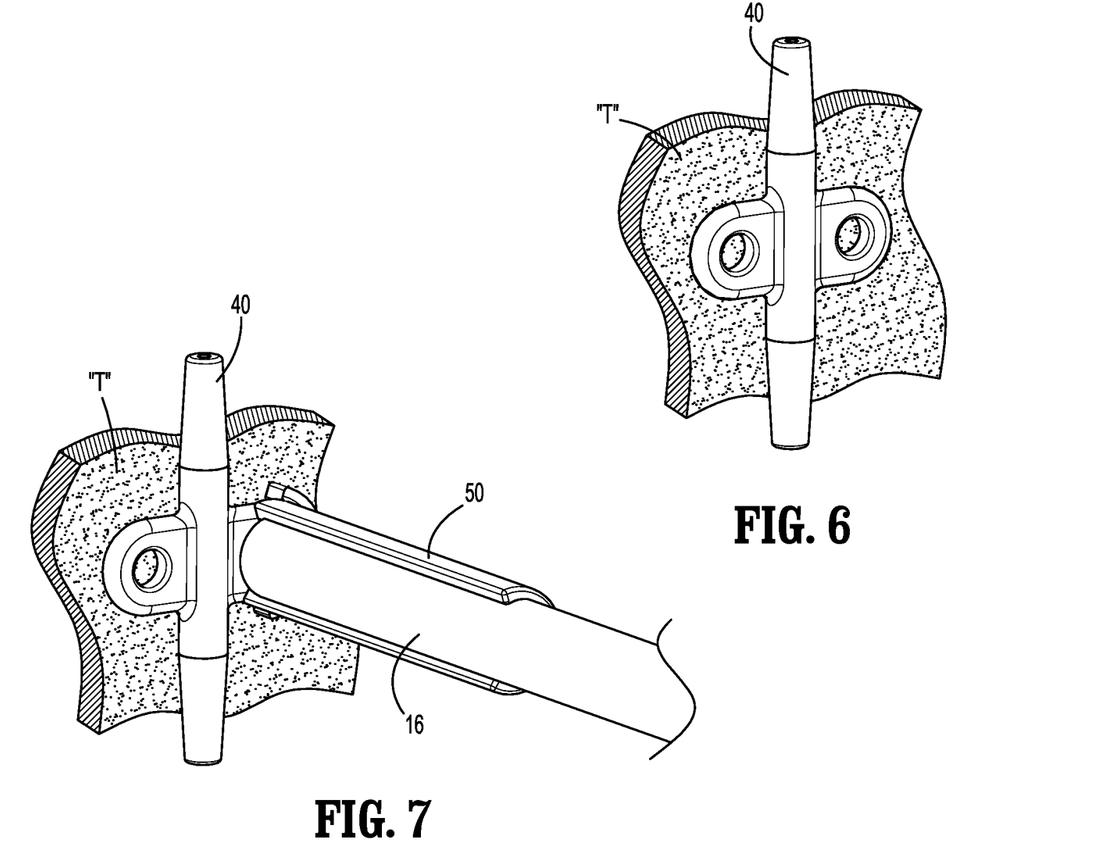
FIGS. 6-8 are progressive views illustrating the surgical instrument system securing the implant to tissue.
Figure 8:
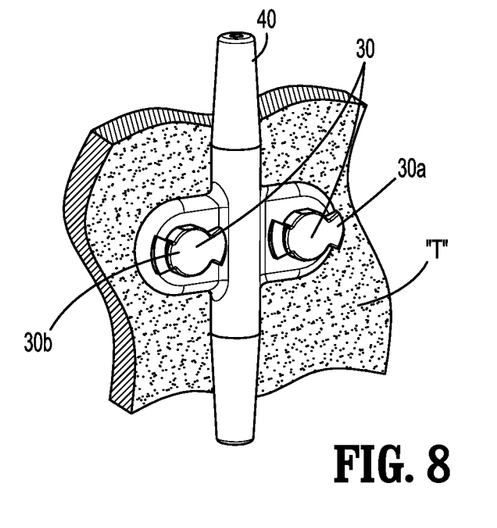

As seen in FIG. 3, implant 40 of the surgical system includes a tubular body 42 having a first wing 44 and a second wing 46 that extend from opposite sides of tubular body 42. Tubular body 42 of implant 40 may support one or more electrical leads (not shown) for facilitating nerve stimulation. First wing 44 of implant 40 defines a first aperture 44a therethrough and second wing 46 of implant 40 defines a second aperture 46a therethrough. First and second apertures 44a, 46a of respective first and second wings 44, 46 are configured to receive fasteners 30 of surgical fastener applier 10 therethrough such that fasteners 30 contact first and/or second wings 44, 46 to secure implant 40 to tissue "T." Positioning guide 50 of the surgical system can be rotatably positioned on end effector 16 of surgical fastener applier 10, as indicated by arrows "R," so that positioning guide 50 can accommodate first and/or second wings 44, 46 of implant 40 in various orientations relative to tissue "T." First and/or second wings 44, 46, which may have a circular or rounded configuration, may be, additionally and/or alternatively sutured to the tissue "T."

Positioning guide 50 of the surgical system includes an elongated body 52 having a proximal end portion 52a and a distal end portion 52b. Elongated body 52 of positioning guide 50 has an arched configuration (e.g., a C-shaped cross-section along a length of elongated body 52) and defines a passage 52c, which may be in the form of an open channel, to facilitate selective securement to end effector 16 of surgical fastener applier 10 so that end effector 16 is received within passage 52c of positioning guide 50. Although shown as having a C-shaped configuration, elongated body 52 of positioning guide 50 may have any suitable geometrical configuration for receiving and/or accommodating any suitable geometrical configuration of end effector 16 of surgical fastener applier 10. Positioning guide 52 further includes an inner surface 52d that defines passage 52c and an outer surface 52e having a rail 52f that extends longitudinally along elongated body 52 of positioning guide 50.

Positioning guide 50 of the surgical system further includes a distal abutment 54 at the distal end portion 52b of positioning guide 50 that is configured to engage a distal end of end effector 16 of surgical fastener applier 10 for functioning as a limit stop when positioning guide 50 is mounted on end effector 16. Distal abutment 54 of positioning guide 50, which also includes an arched configuration (e.g., C-shaped cross-section), projects radially inward from inner surface 52d of elongated body 52 of positioning guide 50 to act as a limit stop for a distal end portion of end effector 16 of surgical fastener applier 10. Distal abutment 54 defines opening 54a in registration with passage 52c of elongated body 52 of positioning guide 50. Opening 54a of distal abutment 54 is positioned to align with a distal opening 16a of end effector 16 (e.g., concentrically) to enable fasteners 30 of surgical fastener applier 10 to be fired therethrough. Distal abutment 54 includes an inner face 54b on a proximal end thereof and an outer face 54c on a distal end thereof.

Positioning guide 50 of the surgical system further includes an implant guide 56 that extends along a portion of an outer edge of elongated body 52 of positioning guide 50 distal to distal abutment 54 thereof. Implant guide 56 of positioning guide 50 has an arched configuration (e.g., C-shaped) and includes an inner guide surface 56a and an outer surface 56b. Implant guide 56 includes a proximal face 56c and a distal face 56d configured to abut tissue "T." Implant guide 56 extends radially outward of outer surface 52e of elongated body 52 of positioning guide 50 so that proximal face 56c of implant guide 56 is an exposed outer surface. Rail 52f of positioning guide 52 is integrally connected to implant guide 56 to secure implant guide 56 to distal end portion 52b of positioning guide 50. Rail 52f is configured to provide support or strength (e.g., longitudinally) to positioning guide 50. Implant guide 56 is positioned relative to distal abutment 54 so that inner guide surface 56a of implant guide 56 and outer face 54c of distal abutment 54 define a guide channel 58. Guide channel 58 is configured to receive one of first or second wings 44, 46 of implant 40 so that positioning guide 50 enables the respective first or second aperture 44a, 46a of implant 40 to axially align with a central longitudinal axis "L-L" of surgical fastener applier 10 (e.g., concentrically) for facilitating securement of fasteners 30 and implant 40 to tissue "T."

In use, with positioning guide 50 mounted on end effector 16 of surgical fastener applier 10 and oriented in a first direction to accommodate first wing 44 of implant 40, first wing 44 of implant 40 can be received in guide channel 58 of positioning guide 50 so that a first fastener 30a of surgical fastener applier 10 can be fired through first aperture 44a of first wing 44 and into tissue "T." Positioning guide 50 can then be rotated about end effector 16, as indicated by arrows "R" (FIG. 2), so that implant guide 56 of positioning guide 50 is oriented in a second direction, which may be opposite to the first direction (e.g., 180 degree rotation), to accommodate second wing 46 of implant 40. In this position, second wing 46 can be received in guide channel 58 of positioning guide 50 so that a second fastener 30b of surgical fastener applier 10 can be fired through second aperture 46a of second wing 46 and into tissue "T" to further secure implant 40 to tissue "T." The positioning guide 50 can be removed from surgical fastener applier 10 as desired. The positioning guide 50 can be disposable and/or reusable.

By way of example, implant 40 may be an anchor for positioning a therapy device within a desired location of the patient. The desired location may be within or along a spinal canal or cord of a patient or along other desired areas within the patient. Such therapy devices can include, for instance, a pacemaker, a defibrillator, a monitoring device, an infusion device, a neurostimulator, a gastric stimulator, a cochlear device, spinal implant or the like.

Figure 9:
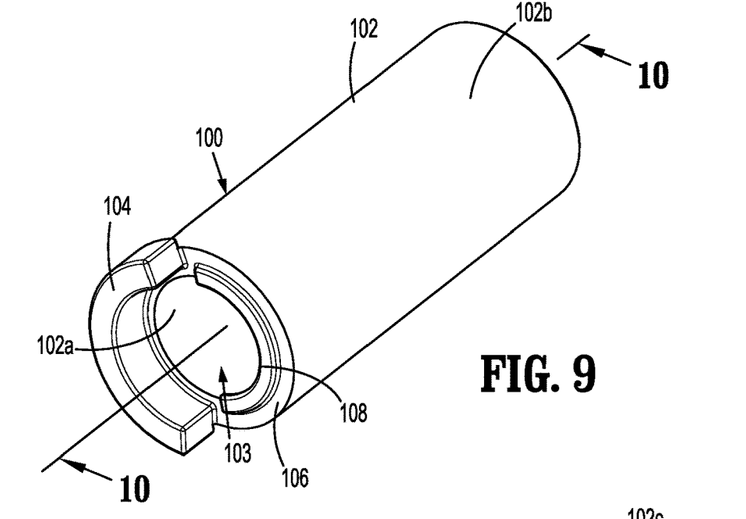
FIG. 9 is a perspective view of another embodiment of a positioning guide in accordance with the principles of this disclosure.
Figure 10:
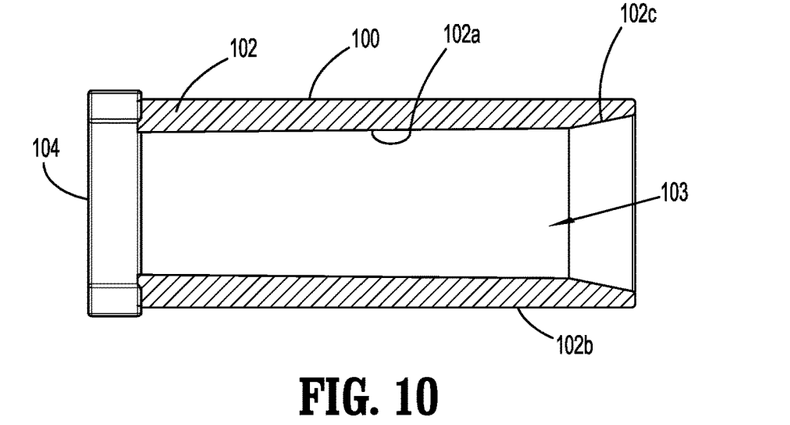
FIG. 10 is a cross-sectional view of the positioning guide of FIG. 9 as taken along section lines 10-10 of FIG. 9.
Figure 11:
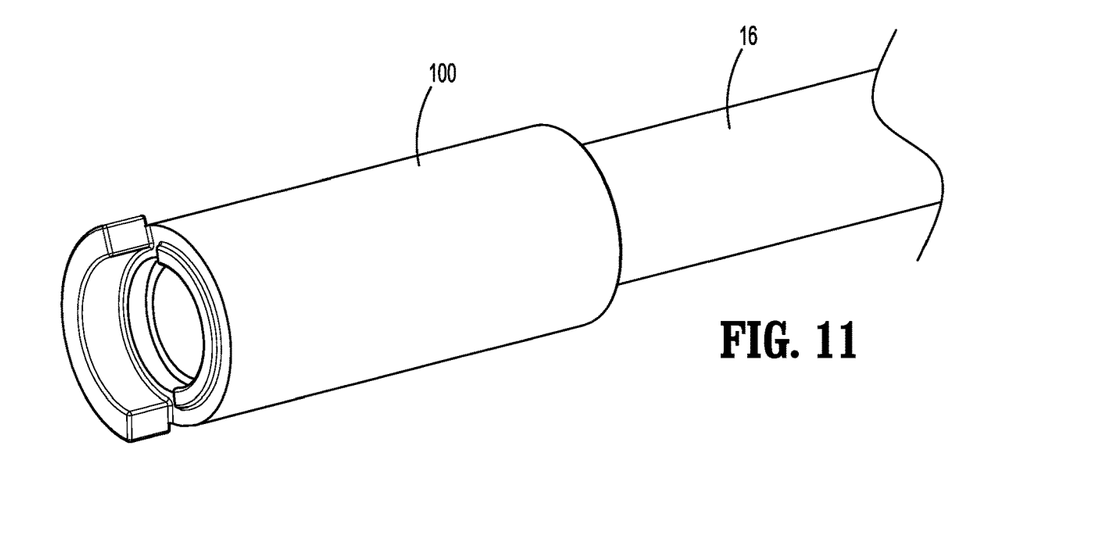
FIG. 11 is a perspective view of the positioning guide of FIG. 9 supported on the surgical instrument of FIG. 1.

With reference to FIGS. 9-11, another embodiment of a positioning guide 100, which may be provided in the form a tubular positioning guide, similar to positioning guide 50, is configured for selective attachment to end effector 16 of surgical fastener applier 10. Positioning guide 100 includes a tubular body 102 supporting an implant guide 104 on a distal end portion thereof. Tubular body 102 of positioning guide 100 includes an inner surface 102a and an outer surface 102b. Inner surface 102a defines a central passage 103 and includes a tapered portion 102c on a proximal end portion thereof to facilitate receipt of a distal end portion of end effector 16 within central passage 103 of positioning guide 100. Positioning guide 100 further includes a distal abutment 106 having a guide rib 108 projecting distally therefrom. Guide rib 108, which may include a reversed C-shape, is disposed in opposed relation with implant guide 104 of positioning guide 100 and includes a reduce profile relative to implant guide 104 to facilitate positioning of implant 40 relative to implant guide 104.

In some embodiments, the disclosed implant guides may be selectively removable from the disclosed positioning guides. For example, implant guide 104 may be selectively secured to positioning guide 100 using any suitable mechanical securement technique such as snap-fit, fastening, adhesive, magnetics, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

Securement of any of the components of the disclosed devices may be effectuated using known securement techniques such welding, crimping, gluing, heat-shrinking, fastening, etc.

Persons skilled in the art will understand that the structures and methods specifically described herein and shown in the accompanying figures are non-limiting exemplary embodiments, and that the description, disclosure, and figures should be construed merely as exemplary of particular embodiments. This disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of this disclosure, and that such modifications and variations are also included within the scope of this disclosure. Accordingly, the subject matter of this disclosure is not limited by what has been particularly shown and described.

What is claimed is:

1. A surgical instrument system, comprising:
    a surgical fastener applier including an end effector configured to support at least one fastener; and
    a positioning guide selectively mountable to the end effector, the positioning guide including an implant guide, the implant guide defining a guide channel configured to receive a portion of an implant to support the implant relative to the end effector to enable the surgical fastener applier to fire the at least one fastener through the implant for securing the implant to tissue.

2. The surgical instrument system of claim 1, wherein the positioning guide includes an elongated body, the implant guide supported on a distal end portion of the elongated body.

3. The surgical instrument system of claim 2, wherein the elongated body includes an arched configuration that defines a passage therethrough positioned to receive the end effector.

4. The surgical instrument system of claim 1, wherein the positioning guide includes a distal abutment configured to act as a limit stop for the end effector when the positioning guide is mounted on the end effector.

5. The surgical instrument system of claim 4, wherein the positioning guide includes a guide rib supported on the distal abutment.

6. The surgical instrument system of claim 1, wherein the implant guide has a C-shaped configuration.

7. The surgical instrument system of claim 1, wherein the positioning guide has a tubular configuration.

8. The surgical instrument system of claim 1, wherein the guide channel is configured to receive at least one wing of the implant.

9. The surgical instrument system of claim 8, wherein the guide channel is configured to position an aperture defined through the at least one wing of the implant so that the aperture receives the at least one fastener therethrough.

10. The surgical instrument system of claim 1, wherein the surgical fastener applier is a tack applier, and wherein the least one fastener includes at least one tack.

11. A positioning guide for a surgical instrument, the positioning guide comprising:
    an elongated body defining a passage therethrough configured to receive an end effector of the surgical instrument therein, the elongated body having a proximal end portion and a distal end portion, the distal end portion supporting an implant guide, the implant guide defining a guide channel configured to receive a portion of an implant to support an aperture of the implant in registration with a longitudinal axis of the end effector.

12. The positioning guide of claim 11, wherein the elongated body includes an arched configuration.

13. The positioning guide of claim 12, wherein the elongated body defines a passage therethrough positioned to receive the end effector.

14. The positioning guide of claim 11, further comprising a distal abutment configured to act as a limit stop for the end effector when the elongated body is mounted on the end effector.

15. The positioning guide of claim 14, wherein the elongated body includes a guide rib supported on the distal abutment.

16. The positioning guide of claim 11, wherein the implant guide has a C-shaped configuration.

17. The positioning guide of claim 11, wherein the elongated body has a tubular configuration.

18. The positioning guide of claim 11, wherein the elongated body includes a rail extending along an outer surface thereof, the rail connected to the implant guide.

19. An endoscopic surgical tack applier system, comprising:
- an endoscopic surgical tack applier including an end effector configured to support at least one tack; and
- a positioning guide selectively removable from the end effector, the positioning guide including an implant guide configured to support an implant adjacent to a distal end portion of the end effector such that an aperture of a wing of the implant is disposed in registration with the at least one tack when the at least one tack is supported by the end effector.

20. The endoscopic surgical tack applier system of claim 19, wherein at least the implant guide includes a C-shaped cross-section.

* * * * *